United States Patent [19]

Huffman

[11] Patent Number: 5,788,489
[45] Date of Patent: Aug. 4, 1998

[54] DENTAL MODEL BASE ASSEMBLY

[76] Inventor: Ronald E. Huffman, Rte. 1, Box 502M, Sapulpa, Okla. 74066

[21] Appl. No.: 482,738

[22] Filed: Jun. 7, 1995

[51] Int. Cl.⁶ .................................................. A61C 11/08
[52] U.S. Cl. ...................................................... 433/60
[58] Field of Search ............................. 433/60, 74, 34, 433/213

[56] References Cited

U.S. PATENT DOCUMENTS

| | | | |
|---|---|---|---|
| 1,745,570 | 2/1930 | Dimelow | 433/202.1 |
| 1,780,117 | 10/1930 | Craigo . | |
| 2,398,671 | 4/1946 | Saffir | 433/208 |
| 2,585,857 | 2/1952 | Schwartz | 433/206 |
| 3,453,736 | 7/1969 | Waltke . | |
| 3,518,761 | 7/1970 | Susman et al. . | |
| 3,937,773 | 2/1976 | Huffman | 264/17 |
| 3,969,820 | 7/1976 | Kulig et al. . | |
| 4,021,916 | 5/1977 | Spalten | 433/74 |
| 4,122,606 | 10/1978 | Roman . | |
| 4,127,939 | 12/1978 | Samuel et al. . | |
| 4,371,339 | 2/1983 | Zeiser | 433/74 |
| 4,382,787 | 5/1983 | Huffman | 433/64 |
| 4,398,884 | 8/1983 | Huffman | 433/74 |
| 4,443,192 | 4/1984 | Blitz | 433/74 |
| 4,449,931 | 5/1984 | Saito | 433/74 |
| 4,459,110 | 7/1984 | Jackson | 433/74 |
| 4,521,188 | 6/1985 | Metzler | 433/74 |
| 4,608,016 | 8/1986 | Zeiser | 433/74 |
| 4,708,835 | 11/1987 | Kiefer | 264/17 |
| 4,721,464 | 1/1988 | Roden et al. | 433/74 |
| 4,767,331 | 8/1988 | Hoe | 433/213 |
| 5,028,235 | 7/1991 | Smith | 433/223 |
| 5,049,075 | 9/1991 | Barrut | 433/196 |
| 5,098,290 | 3/1992 | Honstein et al. | 433/74 |
| 5,197,874 | 3/1993 | Silva et al. | 433/74 |
| 5,352,117 | 10/1994 | Silva | 433/60 |
| 5,466,152 | 11/1995 | Walter | 433/74 |

FOREIGN PATENT DOCUMENTS

| | | | |
|---|---|---|---|
| 866118 | 4/1961 | United Kingdom . | |
| 8810101 | 12/1988 | WIPO | 433/34 |

OTHER PUBLICATIONS

Instruction Booklet, DVA Model & Die System, "Instructions for Use", DVA, Inc.
Instructional Guide, Step by Step, Die-Maker W.O.W. Articulator, Accu Bite, East Lansing, Michigan.
Brochure, "Die-Maker W.O.W. Articulator", Accu Bite.

*Primary Examiner*—Cary E. O'Connor
*Attorney, Agent, or Firm*—Fish & Richardson P.C.

[57] ABSTRACT

A premanufactured dental model base, and method, for supporting a cast dental model where the dental model base has preformed apertures adaptable for securing the dental model to the dental model base and for disengagably retaining the dental model segment of a damaged tooth. The dental model base has a dental model base body which is adaptable for supporting the dental model. The dental model base body may be connected to an articulator attachment bar which is adaptable for engaging a disposable articulator. The dental model base body may alternatively be connected to an articulator attachment plate which is adaptable for connecting the dental model base to a metal articulator. In one embodiment, the articulator attachment plate is detachably engaged to the dental model base body and the articulator attachment bar slidingly engages the dental model base body. Thus, the dental model base may be used with either a metal articulator or a disposable articulator. In another embodiment, the dental model base body has preformed apertures that correspond more closely with normal tooth placement than previous dental model base bodies.

32 Claims, 9 Drawing Sheets

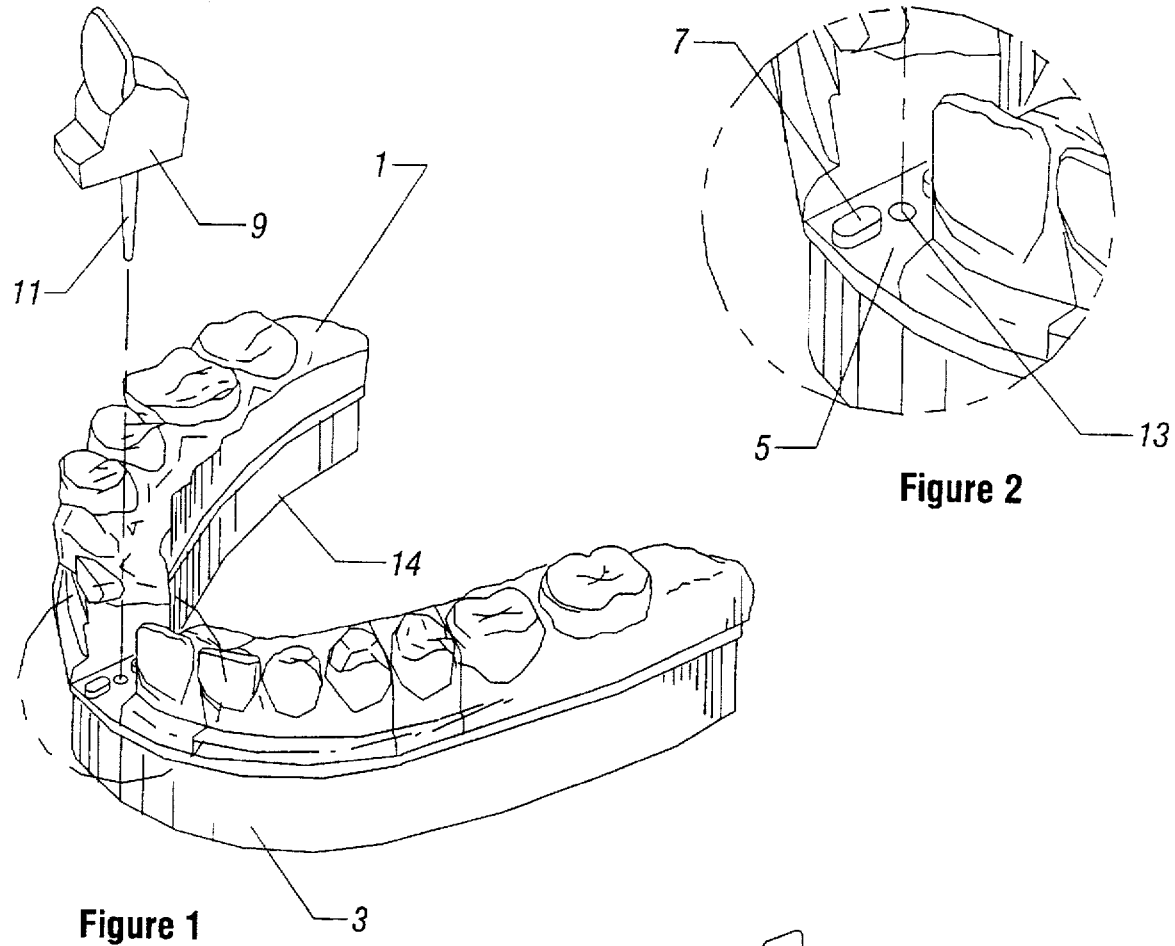
Figure 1
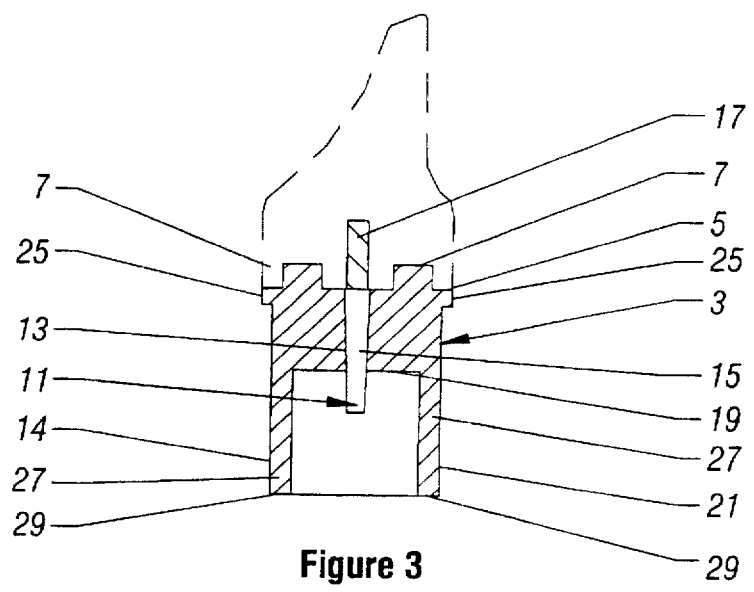
Figure 2
Figure 3

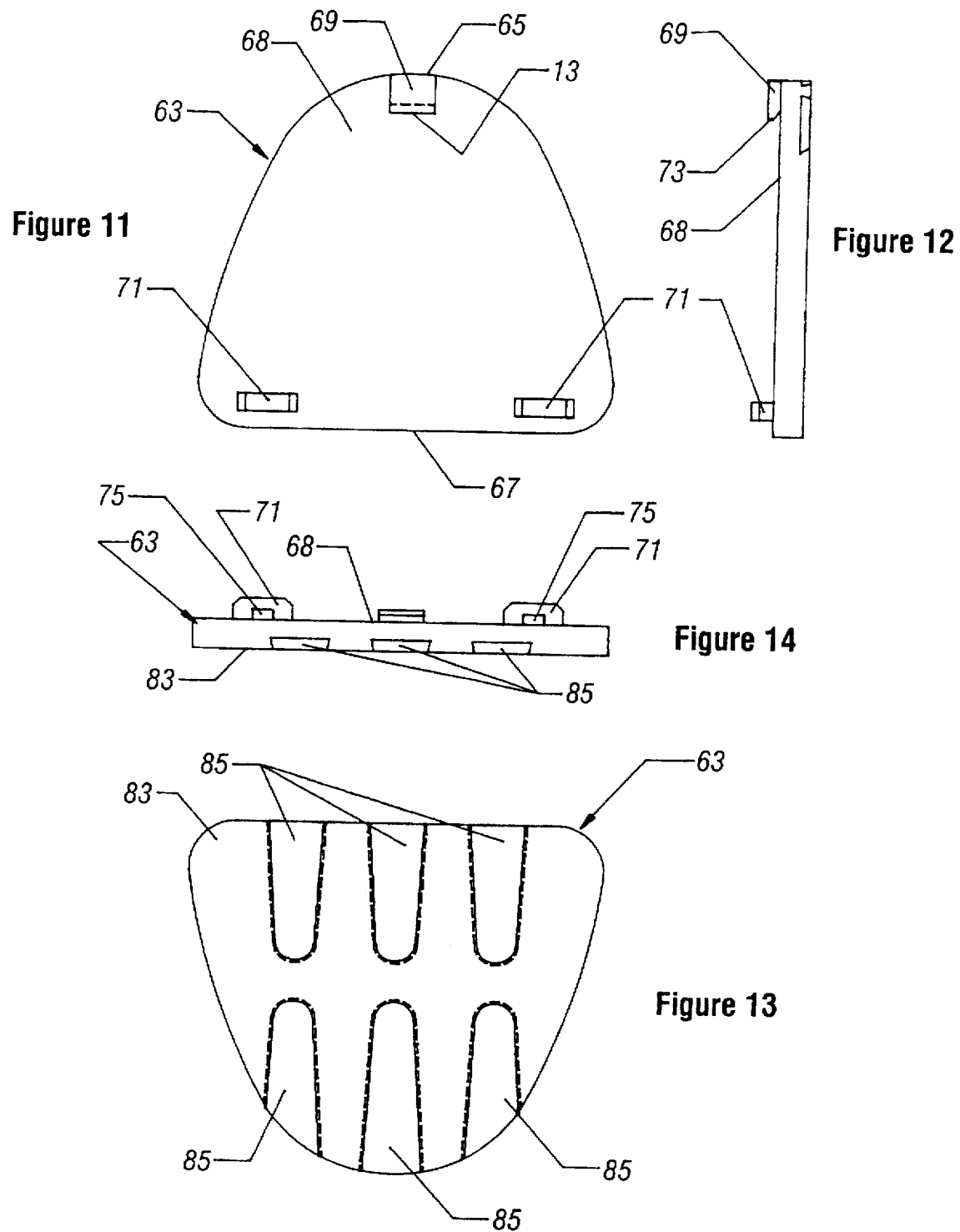

DENTAL MODEL BASE ASSEMBLY

BACKGROUND

This invention relates generally to a dental model base assembly and more particularly to such an assembly in which a premanufactured dental base body having a plurality of apertures may be attached to a disposable dental articulator or a metal articulator.

Damaged teeth may be repaired or replaced by crowns, bridge inlays or other common dental prosthesis. A successful repair requires accurate alignment and visual uniformity of the repaired tooth with the patient's other teeth. Typically, a model is made of the patient's teeth and the prosthesis is fitted to the model and adjusted to achieve proper alignment and visual uniformity.

The model is typically formed by having a patient bite into a pliant casting material which cures to create a mold cavity having a negative impression of the patient's teeth and gums. The mold can be of all or any portion of the patient's gum line. A castable material is then poured into the negative impression to create a stone replica or dental model of the patient's teeth and gums.

To facilitate prosthesis development, the replica of the damaged tooth or teeth is severed from the remainder of the dental model. Severability is achieved by positioning the knurled end of a tapered dowel pin in the uncured stone material in correspondence with the damaged tooth or teeth. The dowel pin or pins must be carefully aligned and held in position which requires skill and time. Once the casting of the gum and teeth has hardened, the cured dental model is positioned adjacent an uncured dental model base which is held in a dental base mold. The tapered portion of the dowel pins protruding from the dental model are positioned in the uncured dental model base. To prevent bonding with the dental model base, wax may be placed between the base and the dental model and around the tapered portion of the dowel pins.

Once the dental model base has cured, a saw cut on each side of the damaged tooth model is made down to the dental model base which allows removal of the damaged tooth model and the attached dowel from the rest of the dental model.

Once the damaged tooth model is removed, the prosthesis can be fitted and adjusted without the spacial limitations encountered when the damaged tooth model is joined to the full dental model. After the prosthesis is made and attached to the dental model segment, the tapered dowel attached to the dental model segment is guided into its respective aperture in the dental model base which guides the dental model segment to its position in the dental model. Alignment and visual conformity are then assessed.

Alignment is ascertained by evaluating the registration of the repaired tooth with the dental model of the patient's opposing teeth. This is achieved by connecting the upper and lower dental model with an articulator. If the prosthesis is out of alignment or does not visually conform to the rest of the patient's teeth, the dental model segment containing the damaged tooth can be removed, adjusted and returned to the dental model base. This process is repeated until proper alignment and visual conformity is achieved. Thus, the model of the damaged tooth may be removed and inserted into the base repeatedly. This repeated removal and reinsertion can damage the fit of the tapered portion of the dowel pin within the cast dental model base which decreases the accuracy of the alignment procedure.

The Vertex® articulator is one disposable articulator typically used to check the alignment of repaired teeth. The Vertex® articulator is glued to a slot in the rear portion of the cast dental model bases. Other typical articulators are metal and the dental model is attached semi-permanently by applying a bonding agent, such as plaster, to the dental model base and the articulator. While metal articulators may be separated at the hinge, protruding portions of the articulator obstruct access to the dental model from certain directions. A technician may prefer using one type of articulator in certain circumstances and the other when the circumstances are different.

The above described process requires time for the dental model and dental model base castings to cure. Also, skill and time are both required to accurately place the dowel pins in the dental model. Any misalignment may result in an unusable casting. Thus, considerable time is spent achieving proper alignment and allowing the dental model base casting to cure.

Some dental model bases are fabricated from plastic. In one version, a technician must drill a tapered aperture in the dental model base to accommodate the placement of the dowel pin in the dental model casting. Skill and time are required to align the dowel pin with the damaged tooth model and the plastic base and to accurately drill the tapered aperture which receives the tapered dowel pin.

Another available plastic dental model base has a plurality of pre-formed apertures for receiving dowel pins which eliminate the above-mentioned drilling step. However, the apertures are not positioned to correspond with normal tooth placement.

Also, in existing full arch plastic bases, plastic extends from the right molars to the left molars, creating a platform for excess casting material in the lingual area. It may be desirable to remove this excess casting material as part of the model preparation process. The plastic platform interferes with this removal step. The platform also may hinder assessment of visual conformity.

In summary, the dowel pins may be accurately aligned with the damaged tooth in a cast dental model base; however, the casting procedure takes time and requires skill. Plastic bases avoid the expense of casting a dental model base but may require additional steps, such as drilling, for accurate placement of a dowel within the dental model. If the plastic base has preformed apertures for dowel placement, the apertures do not correspond to normal tooth placement and skill is required to accurately place the dowels within the dental model. Inaccurate placement of the dowel in a cast or preformed dental model base may result in an unusable dental model as the dental model segment may be unseverable from the dental model.

As mentioned above, metal dowels are typically used to detachably engage a dental model segment to the dental model base. However, metal dowels are undesirable in some circumstances. For example, porcelain facings are often created to repair damaged teeth. The green porcelain material is applied to a damaged tooth model and the dental model segment containing the tooth model is heated to set the porcelain material. This heating temperature is elevated and will adversely affect typical metal dowels.

Therefore, what is needed is a preformed dental model base having preformed apertures. An improved base would have apertures corresponding to normal tooth placement. Such a base would eliminate the need to pour a dental model base while reducing the skill and time required to accurately align the dowels within the dental model. Additional improvements would make the base adaptable for use with a variety of existing articulators, giving technicians the option of using their preferred articulator for each specific case. A further improvement would provide detachable engagement of the dental model base body with the metal articulators, giving technicians greater access to the dental model. Removal of the platform in the lingual area would be an additional improvement, giving technicians improved access to the dental model, facilitating removal of excess casting material in the lingual area and enhancing assessment of visual conformity. Adding additional apertures to the dental model base body anticipating abnormal tooth placement would be another improvement. Still another improvement would provide a dental model base adaptable for supporting a dental model and a dental model segment without using metal dowels.

SUMMARY

The present invention is directed to an apparatus that satisfies the need for a preformed dental model base. In one embodiment, the base is adaptable for use with a variety of existing dental articulators. In another embodiment, the dental model detachably engages a metal articulator. In another embodiment, the dental model is used sequentially with different types of articulators. In yet another embodiment, the preformed apertures in the dental model base body correspond to normal tooth placement. In still another embodiment, additional apertures are provided to anticipate abnormal tooth placement.

The dental model base comprises a premanufactured dental model base body. The base body has a plurality of performed apertures that extend from a dental model support surface into the dental model base body. An articulator attachment bar is connectable to one end of the dental model base body.

In another embodiment, a plate engagement surface is opposite the dental model support surface of the base body. The plate engagement surface is detachably connectable to an articulator attachment plate.

In yet another embodiment, the apparatus comprises the dental model base body detachably connected to an articulator attachment bar and an articulator attachment plate as described above.

In another embodiment, the apertures within the dental model base body are positioned to correspond with normal tooth placement. In yet another embodiment, additional apertures can be preformed in the dental model base body to correspond with the probable position of teeth that are not in their normal position. In still another embodiment, the dental model base body has apertures adaptable for forming stone dowels such that metal dowels are unnecessary.

Some advantages provided by these embodiments are:

1. Time savings resulting from not casting the dental base;
2. Preformed apertures corresponding to normal tooth placement facilitate proper pin placement in the dental model, thereby saving time and requiring less skill;
3. Adaptability for use with a disposable articulator such as the Vertex® articulator;
4. Adaptability for use with a metal articulator;
5. A full arch base body having a convenient U-shape which allows for removal of excess casting material in the lingual area, improves access to the dental model and enhances assessment of visual conformity;
6. Durable pin/dental base mating surfaces assuring proper alignment with repeated use;
7. A snap-fitting mechanism for use with metal articulators that allows for easy removal of the dental model from the articulator;
8. A shape corresponding to the normal shape of a patient's gum line;
9. A transparent base that aids visual alignment;
10. A rigid plastic base that helps minimize shrinkage of the cast dental model; and
11. A dental model base body adaptable for forming stone dowels, thereby eliminating the need for metal dowels.

Other advantages and features will become apparent from the following description and from the claims.

BRIEF DESCRIPTION OF THE DRAWINGS

FIG. 1 is a perspective view of a full arch dental model base according to the present invention supporting a dental model.

FIG. 2 is an enlarged perspective view of a portion of a full arch dental model base according to the present invention.

FIG. 3 is a cross-sectional view of a full arch dental model base according to the present invention supporting a dental model.

FIG. 11 is a top plan view of an articulator attachment plate as used in an embodiment of the present invention.

FIG. 12 is a side elevation view of an articulator attachment plate according to the present invention.

FIG. 13 is a bottom plan view of an articulator attachment plate according to the present invention.

FIG. 14 is a rear elevation view of an articulator attachment plate according to the present invention.

DESCRIPTION OF THE PREFERRED EMBODIMENTS

Figure 4:
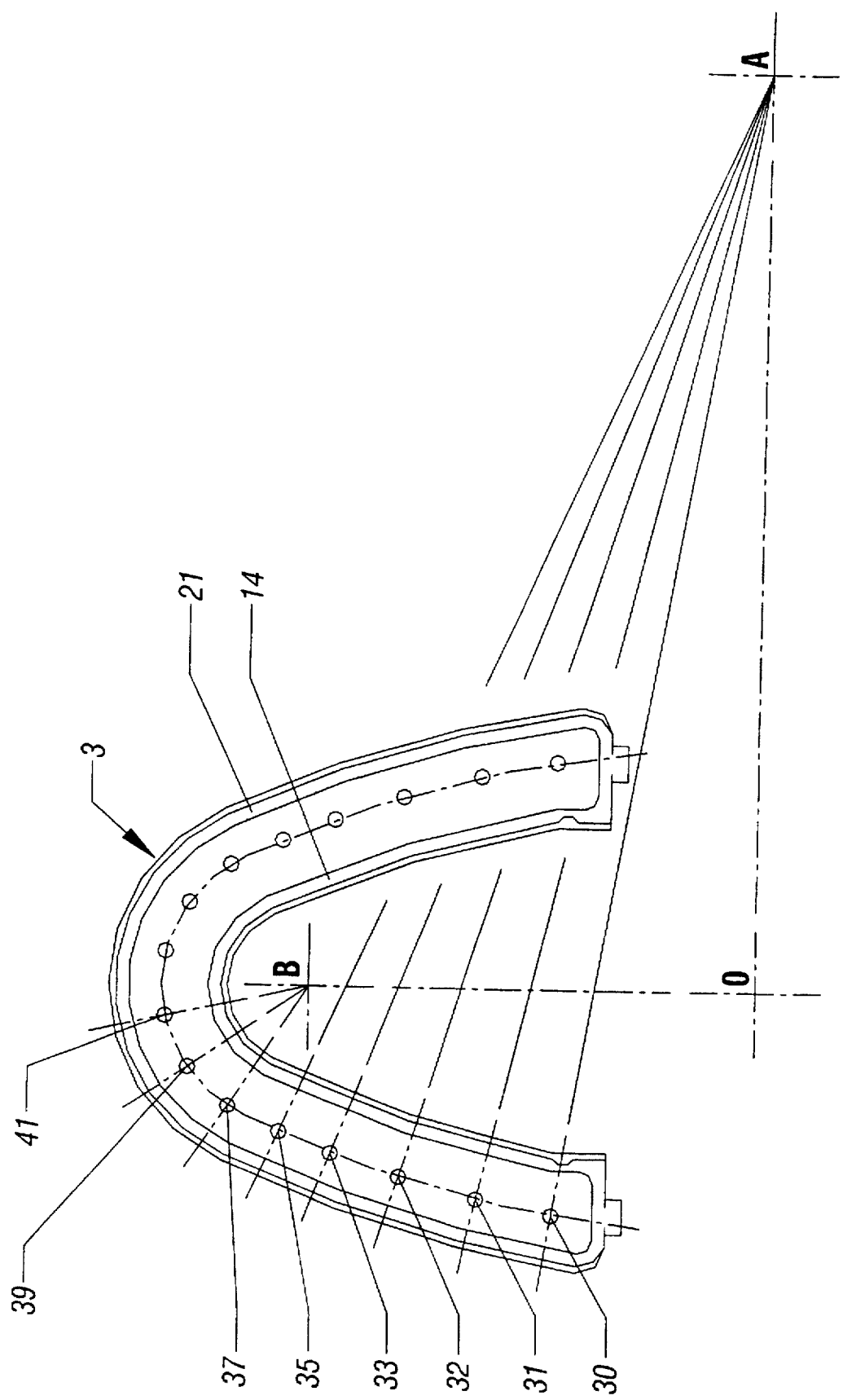
FIG. 4 is a plan view of a full arch medium size upper dental model base according to the present invention with the center of normally positioned teeth designated.

FIG. 1 depicts a full arch dental model 1 supported by one embodiment of a dental model base body 3 according to the present invention. In this embodiment, a clear acrylic plastic is preferred, however, many other materials may be used. As shown in FIG. 2, the dental model 1 is adjacent the dental model support surface 5 which defines one surface of the dental model base body 3. The dental model support surface 5 has indexing protrusions 7 extending from the dental model support surface 5 into the dental model 1. Saw cuts through the dental model 1 on either side of the model of a damaged tooth allow removal of a dental model segment 9. The tapered portion of a dowel 11 is fixed to the dental model segment 9 and is detachably engaged with a tapered aperture 13 in the dental model base body 3. In this embodiment, the dental model base body 3 has an interior wall 14. The interior wall 14 is U-shaped and the lingual area is unobstructed.

FIG. 3 depicts a dowel 11 engaging a tapered aperture 13 that extends from the dental model support surface 5 into the dental model base body 3. The dowel 11 has a tapered end 15 and a knurled end 17. The tapered end 15 corresponds generally to the shape of the aperture 13, to facilitate insertion and removal of the dowel 11 into and from the aperture 13. The knurled feature enhances the bonding of the dowel to the dental model 1 or dental model segment 9. The tapered dowel 11 maintains the general spacial relationship of the dental model segment 9 relative to the dental model 1. Indexing protrusions 7 extend from the dental model support surface 5 into the dental model 1 to maintain the proper orientation of the dental model segment 9 about the axis of the tapered dowel 11. The indexing protrusions 7 can be of any configuration sufficient to maintain alignment of the dental model segment 9.

The dental model base body 3 has a first surface 19, an exterior wall 21 and an interior wall 14. The dental model support surface 5 extends beyond the interior wall 14 and the exterior wall 21 to form dental model support flanges 25.

The first surface 19 is generally parallel with the dental model support surface 5 and is perpendicular to the interior and exterior walls 14 and 21. The exterior wall 21 and the interior wall 14 extend beyond the first surface 19 to form dowel protection flanges 27 which have plate engagement surfaces 29. The dowels 11 extend through the dental model base body 3 and beyond the first surface 19 but, preferably, do not extend beyond the plate engagement surfaces 29. This facilitates desired disengagement of the dowels 11 by simply applying pressure to the exposed end of the dowel while the dowel protection flanges 27 protect against inadvertent disengagement of the dowels 11.

Through analysis of many dental models, it was discovered that certain geometric relationships exist in normal tooth placement. This discovery permits the arrangement and location of apertures in a dental model base body to more closely conform to the actual location of teeth in a dental model. It has been determined that the normal buccal and lingual walls generally tend to have the same curvatures. Normally, teeth are also generally located at the same point along the gum. However, tooth position may vary along the gum if one or more natural teeth are absent or if other abnormalities exist. While the curvature of the buccal and lingual wall remains fairly constant, the size of the gum varies. It has been determined that most gums can be characterized as small, medium or large. The probable location of teeth along a normal gum can be determined by measuring the location of the center of teeth from a sampling of dental models with gums in the desired size range. The measurements are then averaged to determine the average or normal position of teeth in the sample.

FIG. 4 depicts a bottom view of a dental model base body 3 with a designation of the normal placement of the center of upper teeth on a medium-sized gum. The placement of normal teeth along a gum can be defined by certain points, lines, angles and dimensions, as follows. Points A and B are center points of radii useful for designating normal teeth placement. Line AO is perpendicular to line BO. Point O defines the intersection of lines AO and BO. Line BO bisects the dental model base body 3. Point A is 4.4668 inches to the right of point O. The normal third molar center 30 is found by extending an arc with a 5.6598 inch radius from point A at a 9.75° angle clockwise from line AO and to the left of point A. The normal second molar center 31 is located by extending an arc with a 5.6598 inch radius from point A at a 13.50° angle clockwise from line AO and to the left of point A. The normal first molar center 32 is located by extending an arc with a 5.6598 inch radius from point A at an angle of 17.5° clockwise from line AO and to the left of point A. The normal second bicuspid center 33 is found by extending an arc with a 5.6598 inch radius from point A at a 21° angle clockwise from line AO and to the left of point A. The normal first bicuspid center 35 is found by extending an arc with a 5.5698 inch radius from point A at a 23.75° angle clockwise from line AO and to the left of A. Point B is 2.1443 inches up from point O along line BO. The normal cuspid center 37 is found by extending a 0.7054 inch radius from point B at an angle of 123° clockwise from and to the left of line BO. The normal lateral incisor center 39 is found by extending a 0.7054 inch radius from point B at a 145° angle clockwise from and to the left of line BO. The normal central incisor center 41 is found by extending an arc of a length of 0.7054 inches from point B at a 167° angle clockwise from and to the left of line BO. These dimensions define the placement of apertures for the left side of a full arch dental model base body 3. The right side is a mirror image of the left side; therefore, the same geometric relationship is used to define aperture placement on the right side as well.

The exterior wall 21 is located approximately ¼ inches beyond the centerline of the teeth as defined above. The interior wall 14 is located approximately 5/16 inches to the interior of the centerline of the teeth as defined above.

Figure 5:
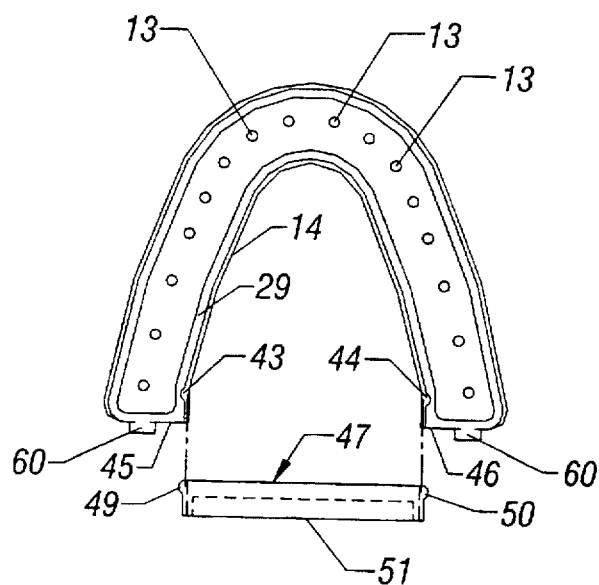
FIG. 5 is an exploded bottom plan view of a dental model base according to the present invention.

In a more detailed aspect of the invention, the dental model base body 3 is adaptable for use with either a disposable articulator, such as the Vertex® articulator, or a traditional metal articulator. FIG. 5 depicts a bottom plan view of this aspect of an embodiment of the invention. The center of the apertures 13 correspond to the normal upper tooth position in a medium sized mouth as depicted in FIG. 3. First and second base attachment grooves 43 and 44 are located near the first and second ends 45 and 46 of the dental model base body 3. The base attachment grooves 43 and 44 extend from the plate engagement surface 29 along the interior wall 14 of the dental model base body 3 in a direction perpendicular to the dental model support surface 5. In this embodiment, the base attachment grooves 43 and 44 do not intersect the dental model support surface 5.

Figure 7:
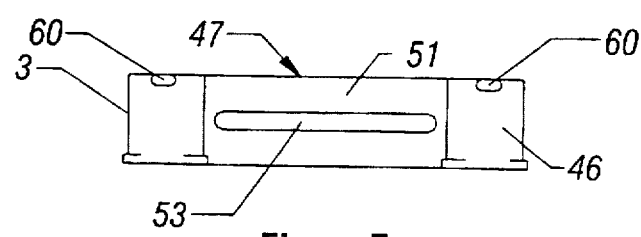
FIG. 7 is a rear elevation view of a dental model base according to the present invention.

FIGS. 4, 5, 6, and 7 depict an articulator engagement bar 47 having first and second base engagement tongues 49 and 50, located on each side of the bar 47. These base engagement tongues 49 and 50 slidingly engage the dental model base attachment grooves 43 and 44 as shown in FIG. 7. As depicted in FIG. 5, the base engagement tongues 49 and 50 are eccentrically disposed on the articulator engagement bar 47 to prevent inadvertent misassembly. The articulator engagement bar 47 also has a posterior articulator engagement surface 51 and an articulator engagement groove 53 in surface 51, for purposes explained below.

Figure 8:
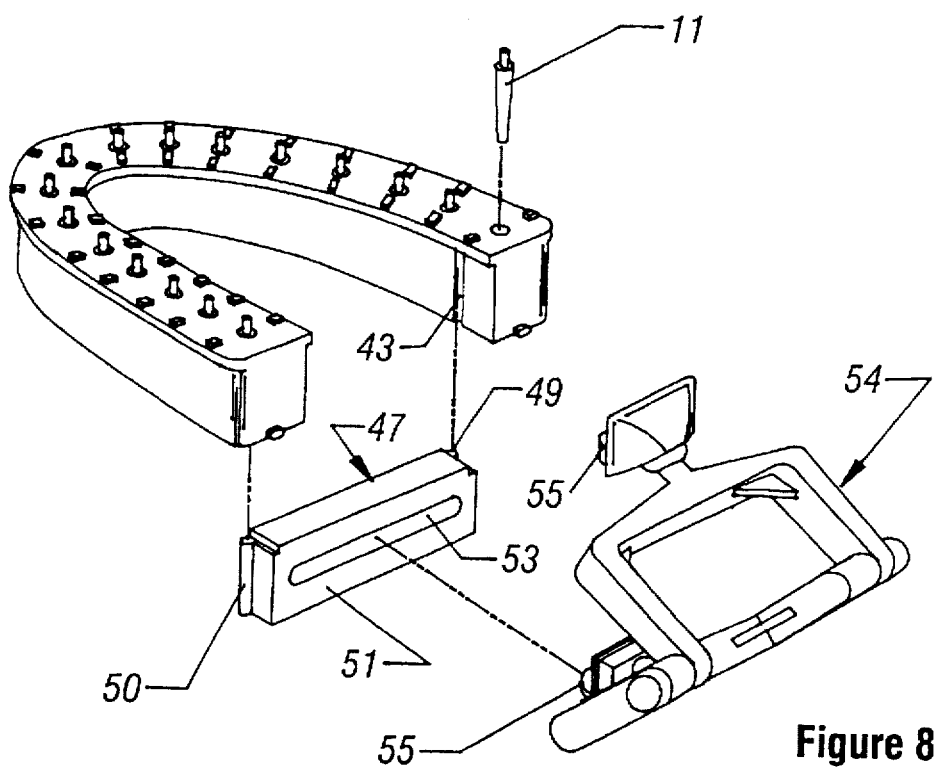
FIG. 8 is an exploded perspective view of a dental model base according to the present invention and a Vertex® articulator.
Figure 9:
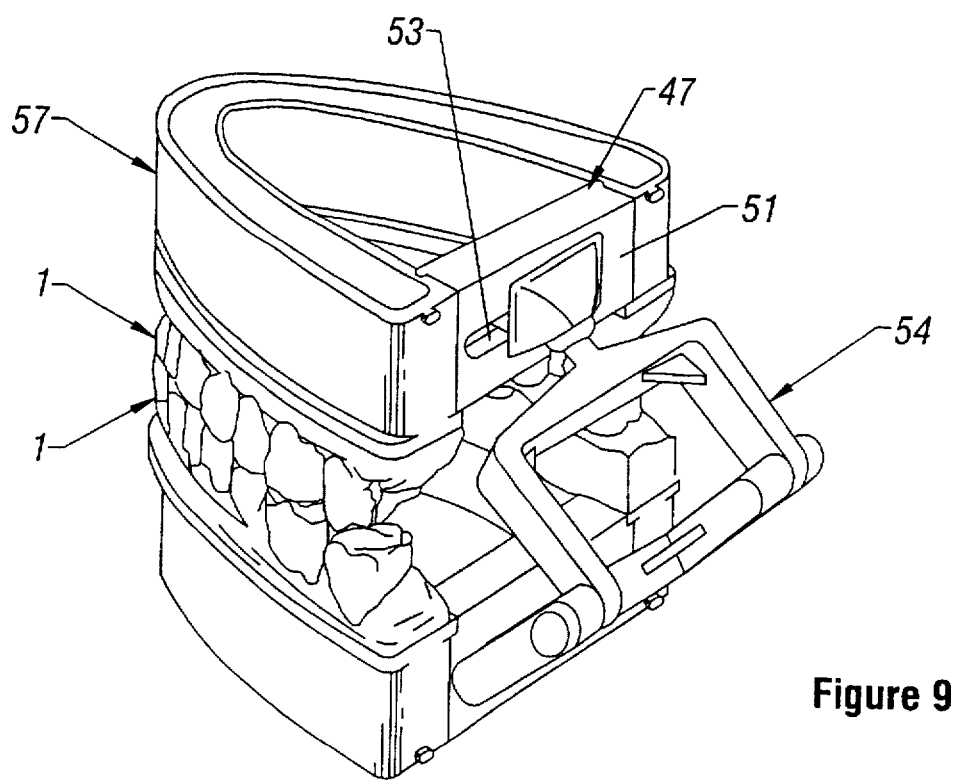
FIG. 9 is a perspective view of two dental model bases supporting dental models according to the present invention connected to a Vertex® articulator.

FIGS. 8 and 9 depict a Vertex® articulator 54 as used with an embodiment of the invention. The articulator engagement bar 47 has base engagement tongues 49 and 50 that slidingly engage the base attachment grooves 43 and 44 (not shown). Once engaged, the articulator engagement bar 47 may be fixed to the dental model base body 3 by methods, such as gluing, customarily used in dental labs. The Vertex® articulator 54 has a pair of articulator tongues 55 which slidingly engage the articulator engagement groove 53. Once engaged, the Vertex® articulator 54 may be attached to the articulator engagement bar 47, by any appropriate adhesive customarily used in dental labs. Once attached to the disposable articulator 54, the dental model base 57 and attached dental models 1 may be manipulated to check for proper registration.

Some technicians may prefer to use a metal articulator, for certain applications of the present invention. When the dental model base is used with a metal articulator, certain additional, optional features may be employed. A description of these features follows.

Figure 10:
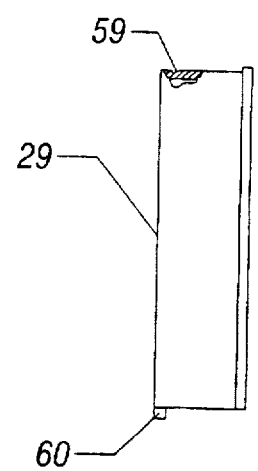
FIG. 10 is a side elevation view of a dental model base body according to the present invention.
Figure 6:
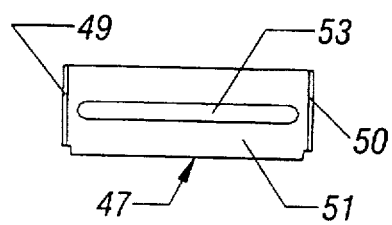
FIG. 6 is an elevation view of an articulator engagement bar as used in an embodiment of the present invention.

As depicted in FIG. 10, a snap groove 59 is formed in the exterior wall 21. At the ends 45 and 46 of the dental model base body 3 are a pair of first securing flanges 60. These optional features permit disengagable attachment of the dental model base body 3 with the articulator attachment plate 63 depicted in FIG. 11.

The articulator attachment plate 63 has a first plate end 65, a second plate end 67 and a dental model base body engagement surface 68. A snap member 69 is near the first plate end 65. Near the second plate end 67 is a pair of U-shaped members 71. The snap member 69 has a snap shoulder 73 which may engage with the snap groove 59 of the dental model base body 3. Each of the U-shaped members 71 has a plate engagement aperture 75 which engage flanges 60 of the dental model base body 3. Engaging the first securing flanges 60 with the U-shaped members 71 and the snap shoulder 73 with the snap groove 59 maintains the articulator attachment plate 63 adjacent the dental model base body 3.

Figure 16:
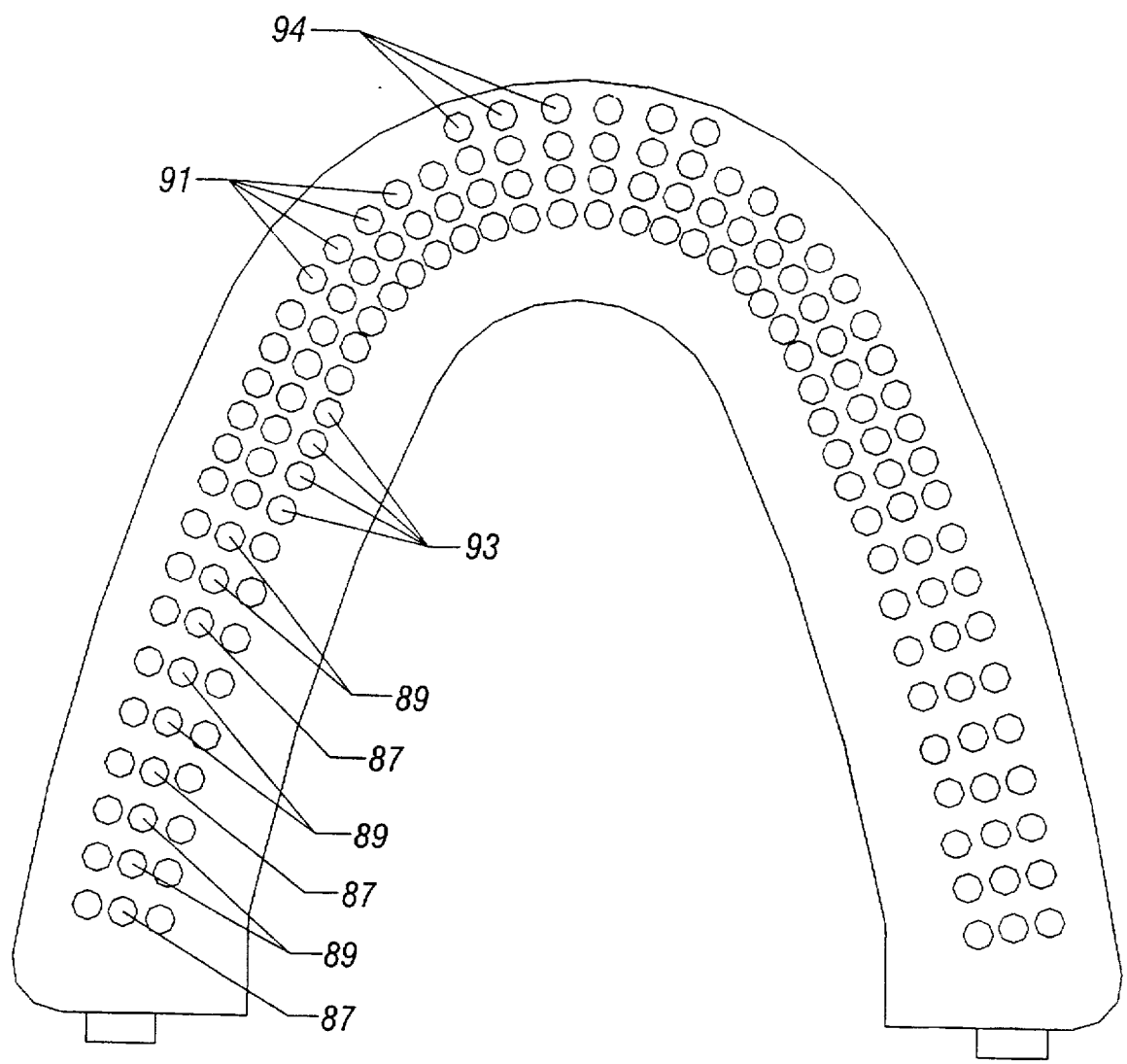
FIG. 16 is a top plan view of an alternative embodiment of a dental model base body according to the present invention.

As seen in FIGS. 13 and 14, opposite the dental model base body engagement surface 68 of plate 63 is an articulator engagement surface 83 having a plurality of recessed anchor cavities 85. The anchor cavities 85 are shaped to securely engage a castable material, such as plaster. Thus, plaster can be applied to the articulator engagement surface 83 and the anchor cavities 85 to attach the articulator attachment plate 63 to a metal articulator 86, as depicted in FIG. 16.

Prior art dental model bases are not easily or quickly disengaged from a metal articulator. While metal articulators 86 may be separated at their hinge, portions of the articulator extend beyond the dental model 1 and may interfere with the required manipulation of the model or prosthesis. In this embodiment of the invention, the dental base body 3 is disengageably attached to the metal articulator, which permits unobstructed access to the dental model 1 by the technician.

Figure 15:
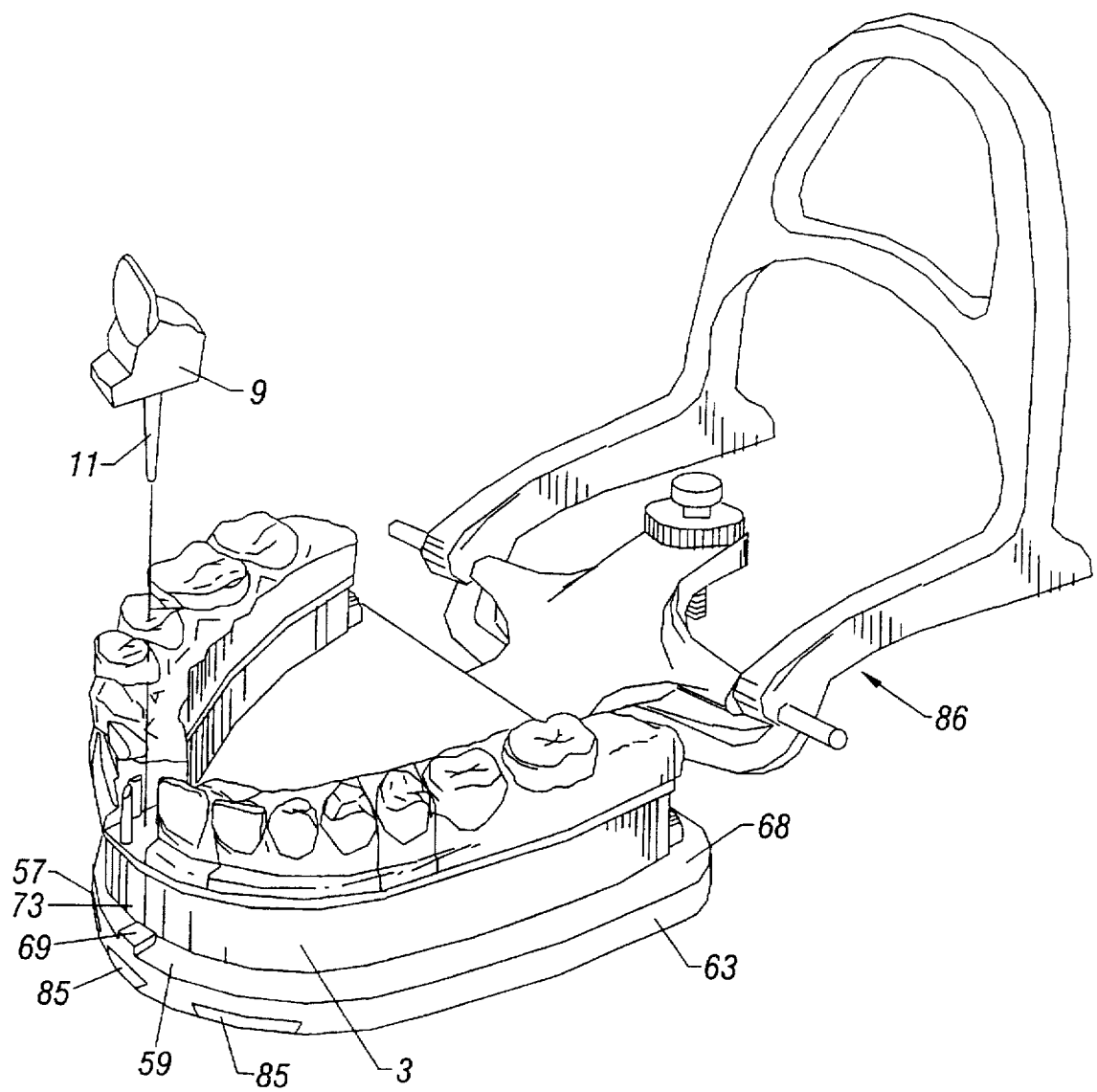
FIG. 15 is an exploded perspective view of a pair of dental model bases according to the present invention as connected to a metal articulator.

In FIG. 15, a dental model base 57 is attached to the lower portion of a metal articulator 86. The first securing flanges 60 slidingly engage the plate engagement apertures 75. The snap shoulder 73 of the snap member 69 engages the snap groove 59. This creates a snap fit between the articulator attachment plate 63 and the dental model base body 3.

In this configuration, a technician may choose to use either the articulator engagement bar 47 to join the dental model base body 3 with a disposable articulator such as the Vertex® articulator or the technician may choose to use the articulator attachment plate 63 to attach the dental model base body 3 to a traditional metal articulator 86. If the dental model base body 3 is used with a Vertex® articulator, the articulator attachment plate is not needed. Similarly, if the dental model base body is used with a traditional metal articulator, the articulator engagement bar is not needed. If a metal articulator 86 is used, the articulator attachment plate 63 is fixed to the metal articulator 86. Anchor cavities 85 facilitate fixation of the articulator attachment plate 63 to the metal articulator 86. The dental model base body 3 may be removed from the metal articulator 86 by simply sliding the snap grove 59 past the snap shoulder 73 and disengaging the first securing flanges 60 from the plate engagement aperture 75.

As mentioned above, FIG. 3 depicts the placement of apertures that correspond to normal tooth placement. However, not all patients have normal tooth placement. Some teeth may migrate along the gum line if, for example, a tooth is removed. Also, some gum lines do not have a normal curvature and, therefore, some teeth may be found outwardly or inwardly from normal tooth placement. To compensate for teeth that are not located at the normal placement positions, additional apertures may be created in the dental model base body.

An embodiment of such a dental model base body is depicted in FIG. 16, where primary apertures 87 correspond to normal tooth placement. Secondary apertures 89 are disposed between the primary apertures 87. In the embodiment depicted, two secondary apertures 89 are disposed between the primary apertures 87 along the normal tooth centerline such that the distance between the primary apertures 87 is equally divided by the secondary apertures 89. Tertiary apertures 91 are located outwardly from the primary apertures 87 and quaternary apertures 93 are disposed inwardly from the primary apertures 87. In this embodiment, the center of the tertiary apertures 91 are located along the radii defining the location of the primary and secondary apertures 87 and 89, approximately 0.10 inches outward from the primary and secondary apertures 87 and 89. The center of the quaternary apertures 93 are located approximately 0.10 inches inwardly from the primary and secondary apertures 87 and 89, along the radii defining the location of primary and secondary apertures 87 and 89. A set of quaternary apertures 94 may be placed outwardly from the tertiary apertures 93 corresponding to incisor placement. Thus, if a patient's teeth are out of alignment with normal tooth placement, dowels may be placed in the secondary apertures 89, tertiary apertures 91 or quaternary apertures 93 and still correspond closely with the center of the displaced tooth.

Figure 17:
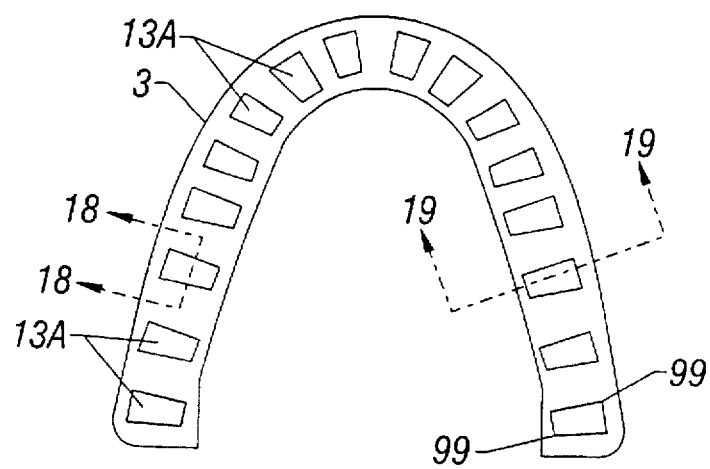
FIG. 17 is a top plan view of an alternative embodiment of a dental model base body according to the present invention.
Figure 19:
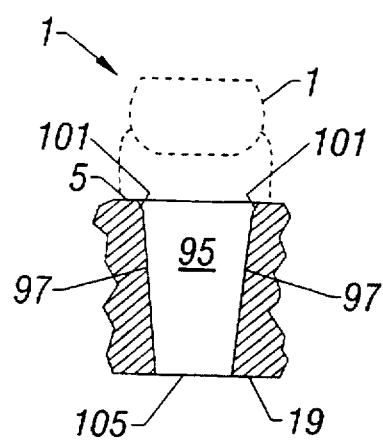
FIG. 19 is a cross-sectional view of a dental model base body supporting a dental model according to the present invention.
Figure 18:
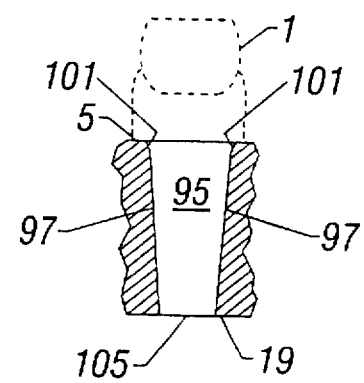
FIG. 18 is a cross-sectional view of the dental model base body of FIG. 16 supporting a dental model according to the present invention.
Figure 20:
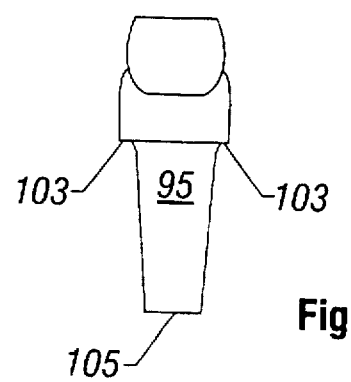
FIG. 20 is a cross-sectional view of a dental model according to the present invention.

As shown in FIG. 17, in another embodiment, the dental model base body 3 has apertures 13A of a noncircular cross section. In this embodiment, the apertures 13A have a cross-sectional area great enough so that the dental model casting material used to form the dental model 1 flows into the aperture to form a cast pin 95 as depicted in FIGS. 18, 19 and 20. In this embodiment, the apertures 13A are positioned in the dental model base 3 to correspond generally with normal tooth placement, as defined in connection with the description of FIG. 3. The apertures 13A have planar side walls 97 that are gradually tapered such that the apertures 13A have a greater cross section at the dental model support surface 5 than at the first surface 19. The apertures 13A have a cross-sectional area near the dental model support surface of about 0.03 square inches. In this embodiment, the planar side walls 97 intersect at curved corners 99.

Similarly, the planar side walls 97 intersect the dental model support surface 5 at curved shoulders 101. The gradual transition from the planar side walls 97 to the dental model support surface 5 creates an arch 103, as shown in FIG. 20, in the dental model, which reduces the probability of a fracture between the cast pin 95 and the dental model 1.

Figures 21, 21A:
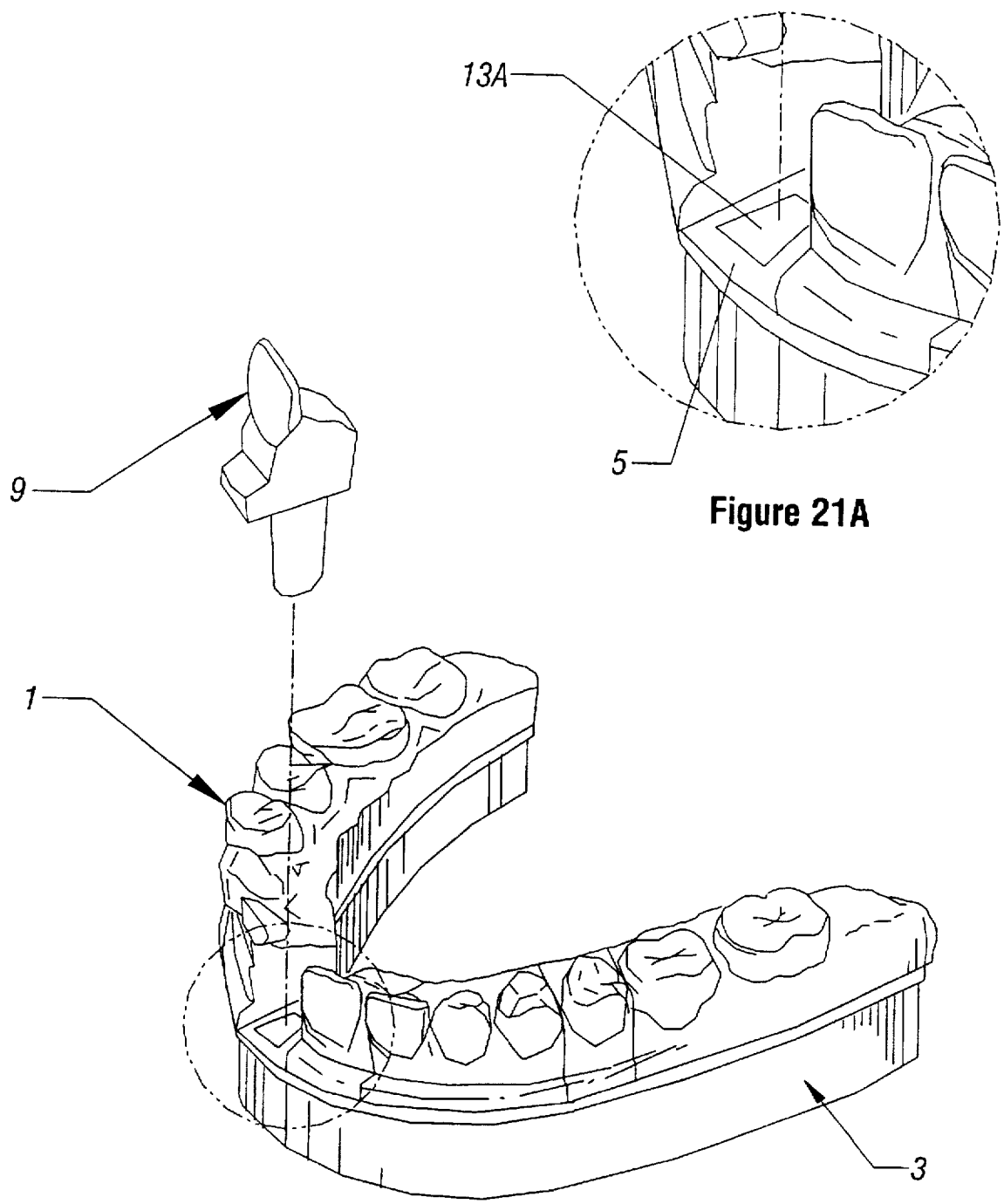
FIG. 21 is an exploded perspective view of a dental model and base according to the present invention.

As seen in FIG. 21, the affected dental model segment can be removed by cutting through the dental model 1 on both sides of the damaged tooth model. Pressure can then be applied to the cast pin first surface 105 to remove the dental model segment 9 from the dental model base body 3. The tapered noncircular apertures 13A insure proper placement and alignment of the dental model segment 9 with the dental model 1 when the dental model segment is returned to the dental model base body 3. The articulation and adjustment procedures described below can be used with the cast pin dental model base body 3.

The various aspects of the present invention may be used, for example, in the following manner. A dental technician may take a dental model base body according to the present invention and align it with the negative mold of a patient's teeth and gum line. If the patient's teeth correspond to normal tooth placement, the primary apertures 87 within the dental model base body will generally correspond with the location of the patient's teeth. If the patient has teeth that do not correspond with normal tooth placement, the technician can choose a secondary aperture 89, tertiary aperture 91 or quaternary aperture 93 that will correspond generally with the center of the aberrational tooth. A tapered dowel 11 will be placed in the aperture corresponding generally with the center of the tooth to be repaired. Tapered dowels 11 may also be placed randomly in other apertures within the dental model base body 3 to secure the cured dental model 1 to the dental model base body 3.

Once the desired dowels have been placed within the apertures, the negative impression can be filled with casting material and the dental model base body 3 is brought adjacent the uncured dental model 1 with the knurled end 17 of the tapered dowels 11 protruding into the uncured casting material. The technician may choose to place wax or some other nonadhesive material between the damaged tooth segment 9 and the dental model base to reduce adhesion of the damaged dental model segment 9 and the dental model base body 3. If the cast pin system is used, the dental model body 3 aligned with the uncured dental model and casting material is flowed into the apertures 13A. Dowels 11 are not used with a cast pin system.

Once the dental model 1 has cured, the dental model base body 3 may be attached to an articulator. In an embodiment of the present invention, the technician may choose to attach the dental model base body 3 to either a disposable articulator, such as the Vertex® articulator 54 or to a metal articulator 86. Indeed, one embodiment of the present invention permits a technician to use both articulators with the same dental model 1. If the technician chooses to use the dental model 1 with a Vertex® articulator 54 alone, the articulator attachment bar 47 is slidingly engaged with the dental model base body 3 and is glued or otherwise held in place. The Vertex® articulator 54 is then glued or otherwise fixed to the articulator attachment bar 47.

If the technician chooses to use the dental model base body with a metal articulator 86, the articulator attachment plate 63 is snap-fitted to the dental model base body 3 and the assembled dental model 1 and base can then be affixed to the metal articulator 86. This is typically done by plastering the articulator attachment plate 63 to the metal articulator 54. Once the articulator attachment plate 63 has been plastered to the metal articulator 86, the dental model base body 3 can be disconnected from the articulator attachment plate 63.

If both articulators are used, the articulator attachment bar 47 is attached to the dental model base body 3 and the articulator attachment plate 63 is attached to the dental model base body 3. The articulator attachment plate 63 may be fixed to the metal articulator 86 and the dental model base body 3 can, thereafter, be disengaged from the articulator attachment plate 63 and attached to the Vertex® articulator 54.

Thus, both articulators may be used to ascertain the alignment of the repaired tooth.

The dental model 1 may be sawed on either side of a damaged tooth, as shown in FIG. 1. The saw-cut extends to the dental model support surface 5. Once the saw-cut has been completed, the dowels 11 supporting the dental model segment 9 of the damaged tooth can be removed by applying pressure to the end of the dowels 11 protruding below the first surface 19. If the cast pin system is used, pressure is applied to the cast pin first surface 105 to remove the dental model segment 9. Once the dental model segment 9 is removed, a prosthesis can be prepared to repair the damaged tooth. After the prosthesis is attached to the dental model segment 9, the dental model segment 9 can be returned to its place in the dental model 1. The dowels 11 or cast pins 95 align the dental model segment 9 generally with the dental model 1. The indexing protrusions 7 engage the indentations formed during the casting process in the dental model segment 9 to assure alignment about the axis of the dowels 11.

Once the dental model segment 9 has been returned to the dental model 11, registration is evaluated and the technician can determine whether the prosthesis conforms visually to the complete dental model 1. If visual conformity is not achieved or if registration or alignment is improper, the dental model segment 9 containing the damaged tooth and prosthesis can be removed and the technician can adjust the prosthesis accordingly. This process is repeated until proper alignment and visual conformity is achieved. As mentioned previously, the technician has the option of using either the metal articulator 86 or a disposable articulator such as the Vertex® articulator 54 in ascertaining alignment, and indeed, may use both articulators during the process if the technician so chooses.

The foregoing describes various embodiments of the claimed invention. The claimed inventions are not limited to the embodiments described above. For example, it is contemplated that the principles of the invention described above can be applied to half arch dental model bases and quadrant dental model bases. Moreover, numerous alternative constructions exist that fall within the claimed invention.

What is claimed is:

1. A premanufactured dental model base comprising:
   a dental model base body having a dental model support surface, said dental model support surface having a first end;
   a plurality of preformed apertures extending into said dental model base body from said dental model support surface; and an articulator attachment bar connected to said dental model base body near said first end, said articulator attachment bar being adaptable for attaching said dental model base body to an articulator.

2. The dental model base of claim 1, wherein:

said apertures are adaptable for forming a cast pin, said cast pin being of sufficient cross-section to independently support a dental model segment.

3. The dental model base of claim 1, wherein:

said apertures are primary apertures located at predetermined positions along said support surface such that said primary apertures generally have a one-to-one correspondence with normal tooth placement.

4. The dental model base of claim 3, additionally comprising:

a plurality of secondary apertures disposed between said primary apertures, said secondary apertures extending from said dental model support surface into said dental model base body.

5. The dental model base of claim 3, additionally comprising:

a plurality of tertiary apertures disposed outwardly from said primary apertures, said tertiary apertures extending from said dental model support surface into said dental model base body.

6. The dental model base of claim 3, additionally comprising:

a plurality of quaternary apertures disposed inwardly from said primary apertures, said quaternary apertures extending from said dental model support surface into said dental model base body.

7. The dental model base of claim 6, additionally comprising:

a plurality of secondary apertures disposed between said primary apertures, said secondary apertures extending from said dental model support surface into said dental model base body;

a plurality of tertiary apertures disposed outwardly from said primary apertures, said tertiary apertures extending from said dental model support surface into said dental model base body.

8. The dental model base of claim 1, additionally comprising:

a plate engagement surface opposite said dental model support surface and an articulator attachment plate, said plate being adjacent said plate engagement surface.

9. The dental model base of claim 8, wherein:

the dental model base body is adapted for supporting a full arch dental model.

10. A premanufactured dental model base comprising:

a dental model base body having a dental model support surface and a plate engagement surface opposite said dental model support surface said dental model base body having a first end and a second end;

a plurality of preformed apertures extending into said dental model base body from said dental model support surface; and an articulator attachment plate adapted for attaching said dental model base body to an articulator, said articulator attachment plate having a dental model base body engagement surface and an articulator engagement surface, said dental model base body engagement surface being adjacent said plate engagement surface, and said articulator attachment plate being detachably connected to said dental model base body at said first and second dental model base body ends.

11. The dental model base of claim 10, wherein:

said apertures are primary apertures generally having a one-to-one correspondence with normal tooth placement.

12. The dental model base of claim 11, additionally comprising:

a plurality of secondary apertures disposed between said primary apertures, said secondary apertures extending from said dental model support surface into said dental model base body.

13. The dental model base of claim 11, additionally comprising:

a plurality of tertiary apertures disposed outwardly from said primary apertures, said tertiary apertures extending from said dental model support surface into said dental model base body.

14. The dental model base of claim 11, additionally comprising:

a plurality of quaternary apertures disposed inwardly from said primary apertures, said quaternary apertures extending from said dental model support surface into said dental model base body.

15. The dental model base of claim 14, additionally comprising:

a plurality of secondary apertures disposed between said primary apertures, said secondary apertures extending from said dental model support surface into said dental model base body;

a plurality of tertiary apertures disposed outwardly from said primary apertures, said tertiary apertures extending from said dental model support surface into said dental model base body.

16. The dental model base of claim 10, additionally comprising:

a means for anchoring said articulator attachment plate to an articulator.

17. The dental model base of claim 16 wherein:

said attachment means is a cavity.

18. The dental model base of claim 10, additionally comprising:

an articulator attachment bar connected to said dental model base body near said first end of said dental model base body.

19. The dental model base of claim 10, wherein:

said apertures are adaptable for forming a cast pin, said cast pin being of sufficient cross-section to independently support a dental model segment.

20. A premanufactured dental model base comprising:

a unitary dental model base body having a dental model support surface;

an interior and exterior wall intersecting said dental model support surface;

a plate engagement surface opposite said dental model support surface, said plate engagement surface being generally parallel with said dental model support surface and generally perpendicular to said interior and exterior walls, said plate engagement surface intersecting said interior wall;

a plurality of preformed apertures extending into said dental model base body from said dental model support surface and;

an articulator attachment plate, said articulator attachment plate being connected to said dental model base body adjacent said plate engagement surface, said articulator attachment plate being retained adjacent said plate engagement surface by a frictional connection with said interior wall.

21. The dental model base of claim 20, wherein:

said apertures are adaptable for forming a cast pin, said cast pin being of sufficient cross-section to independently support a dental model segment.

22. The dental model base of claim 20, wherein:

said dental model base body is adaptable for supporting a full arch dental model.

23. A method for using a premanufactured dental model base comprising the steps of:

aligning a premanufactured dental model base body over a dental model cavity mold, said dental model base body having a first end and a second end, said dental model base body having a dental model support surface, said dental model base body having a plurality of preformed apertures extending into said dental model base body from said dental model support surface;

placing tapered dowels in said apertures corresponding to the teeth to be removed from a dental model to be formed in said dental model cavity mold;

placing tapered dowels in said apertures to secure said dental model to said dental model base body adjacent said dental model support surface;

filling said dental model cavity mold with an uncured casting material;

placing said dental model base body and connected dowels adjacent said uncured casting material with said dowels extending into said uncured casting material and said casting material contacting said dental model support surface;

removing said dental model from said dental model cavity mold after said dental model has cured; and detachably connecting said dental model base body to an articulator attachment means.

24. The method of claim 23, wherein:

said articulator attachment means is an articulator attachment bar.

25. The method of claim 23, wherein:

said articulator attachment means is an articulator attachment plate and additionally comprising the step of retaining said articulator attachment plate adjacent said dental model base body with connections at said first and second ends.

26. A premanufactured dental model base comprising:

a dental model base body having a dental model support surface;

an interior and exterior wall intersecting said dental model support surface; said interior wall defining an unobstructed lingual area;

a plurality of preformed apertures extending into said dental model base body from said dental model support surface;

a plate engagement surface opposite said dental model support surface, said plate engagement surface being generally parallel with said dental model support surface, said plate engagement surface intersecting said interior and exterior walls; and an articulator attachment plate, said articulator attachment plate being connected to said dental model base body adjacent said plate engagement surface, said articulator attachment plate being retained adjacent said plate engagement surface by a frictional connection with said interior and exterior walls.

27. The dental model base of claim 26 wherein:

said apertures are adapted for forming a cast pin, said cast pin being of sufficient cross-section to independently support a dental model segment.

28. The dental model base of claim 26 wherein:

said dental model base body is adapted to support a full arch model.

29. An apparatus for use in making a dental replica comprising:

a premanufactured dental model base body having a dental model support surface, said dental model base body having a first end and a second end;

a plurality of preformed apertures extending from said dental model support surface into said dental model base body;

a cast dental model adjacent said dental model support surface; and an articulator attachment plate, said articulator attachment plate being retained adjacent said dental model base body with connections at said first end and said second end.

30. The apparatus of claim 29 wherein:

said dental model base body has an interior wall and an exterior wall said interior and exterior walls being perpendicular to said dental model support surface;

said interior and exterior walls being adjacent said dental model support surface; and said interior wall defining an unobstructed lingual area.

31. The apparatus of claim 30 wherein:

said dental model base body supports a full dental arch.

32. The apparatus of claim 30 wherein:

said articulator attachment plate is retained adjacent said dental model base body by frictionally engaging said dental model base body exterior wall.

* * * * *

UNITED STATES PATENT AND TRADEMARK OFFICE
CERTIFICATE OF CORRECTION

PATENT NO. : 5,788,489

DATED : AUGUST 4, 1998

INVENTOR(S) : HUFFMAN

It is certified that error appears in the above-identified patent and that said Letters Patent is hereby corrected as shown below:

Col. 7, line 52: "FIG. 16" should read --FIG. 15--

Col. 8, line 16: "snap grove" should read --snap groove--

Col. 10, line 5: "articulator 54" should read --articulator 86--

Col. 10, lines 17-18: no new paragraph before "Thus,"

Col. 14, line 35, claim 29: "plate," should read --plate; and--

Col. 14, line 35, claim 29: new paragraph after "plate; and"

Col. 14, line 36, claim 29: "being" should read --is--

Signed and Sealed this

Fifteenth Day of February, 2000

*Attest:*

Q. TODD DICKINSON

*Attesting Officer*   *Commissioner of Patents and Trademarks*